United States Patent [19]

Patterson James A.

[11] Patent Number: 4,860,577

[45] Date of Patent: Aug. 29, 1989

[54] OSMOTIC APPLICATIONS OF HOLLOW FIBERS

[75] Inventor: Patterson James A., Sarasota, Fla.

[73] Assignee: Southeastern Illinois College Foundation, Harrisburg, Ill.

[21] Appl. No.: 294,480

[22] Filed: Jan. 6, 1989

[51] Int. Cl.⁴ .................................... G01N 13/04
[52] U.S. Cl. ............................... 73/64.3; 73/714
[58] Field of Search ........................ 73/643, 714

[56] References Cited

U.S. PATENT DOCUMENTS

| | | | |
|---|---|---|---|
| 3,063,288 | 11/1962 | Reiff | 73/64.3 |
| 4,015,462 | 4/1977 | Greyson et al. | 73/64.3 X |
| 4,245,495 | 1/1981 | Kakiuchi et al. | 73/64.3 |
| 4,475,556 | 10/1984 | Reiff | 73/64.3 X |
| 4,481,808 | 11/1984 | Sakata et al. | 73/64.3 X |

FOREIGN PATENT DOCUMENTS 1158901 5/1985 U.S.S.R. ................ 73/64.3

*Primary Examiner*—Daniel M. Yasich
*Attorney, Agent, or Firm*—Limbach, Limbach & Sutton

[57] ABSTRACT

An osmometer for use in the measurement of gases, liquids and solids is disclosed. The osmometer includes a semipermeable hollow fiber, capable of passing liquids but not dissolved solids. The hollow fiber contains a media component with a predetermined osmolarity compatible with the sample to be measured. A gas volume is also contained within the hollow fiber and a sensor is present and located adjacent to the gas volume. The sensor is responsive to changes in the gas or media volume due to changes in the media component caused by the influx or efflux of water to the hollow fiber.

14 Claims, 4 Drawing Sheets

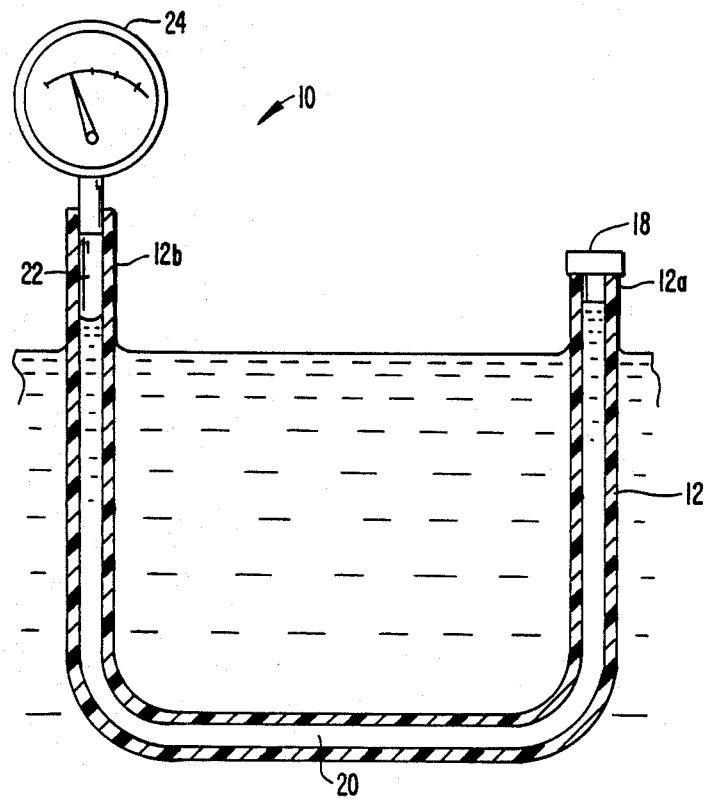
FIG._1.
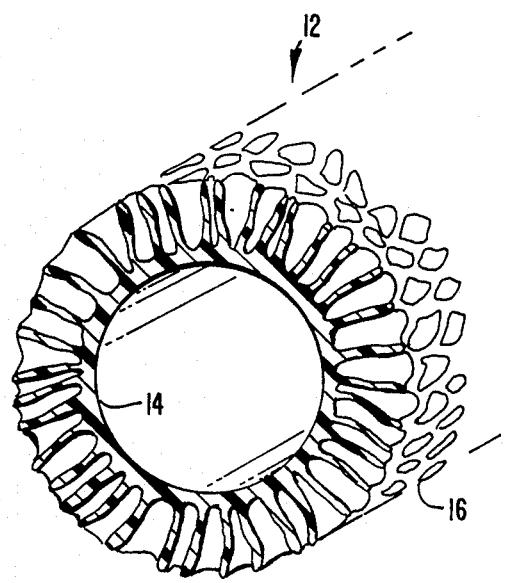
FIG._2.

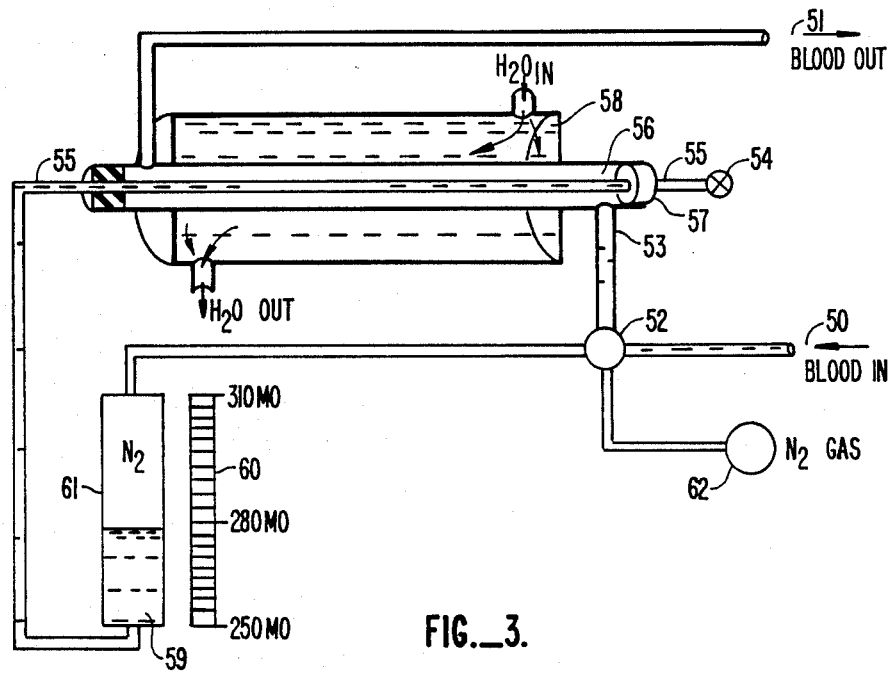
FIG._3.
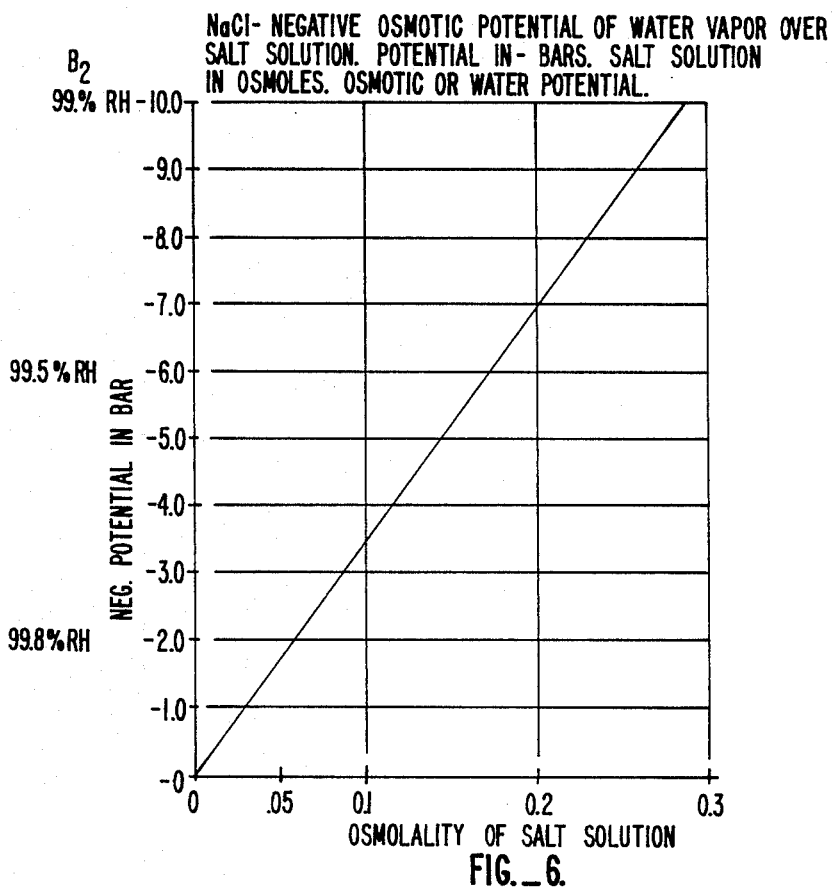
FIG._6.

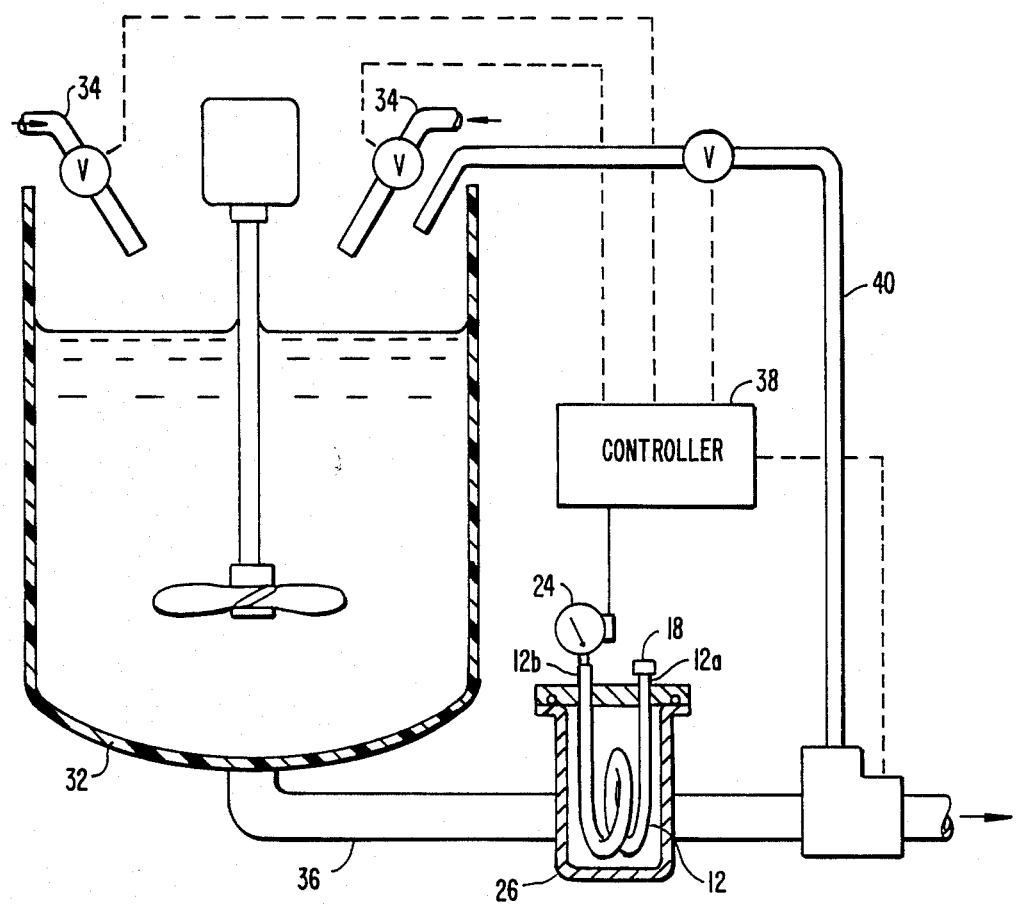
FIG._4.

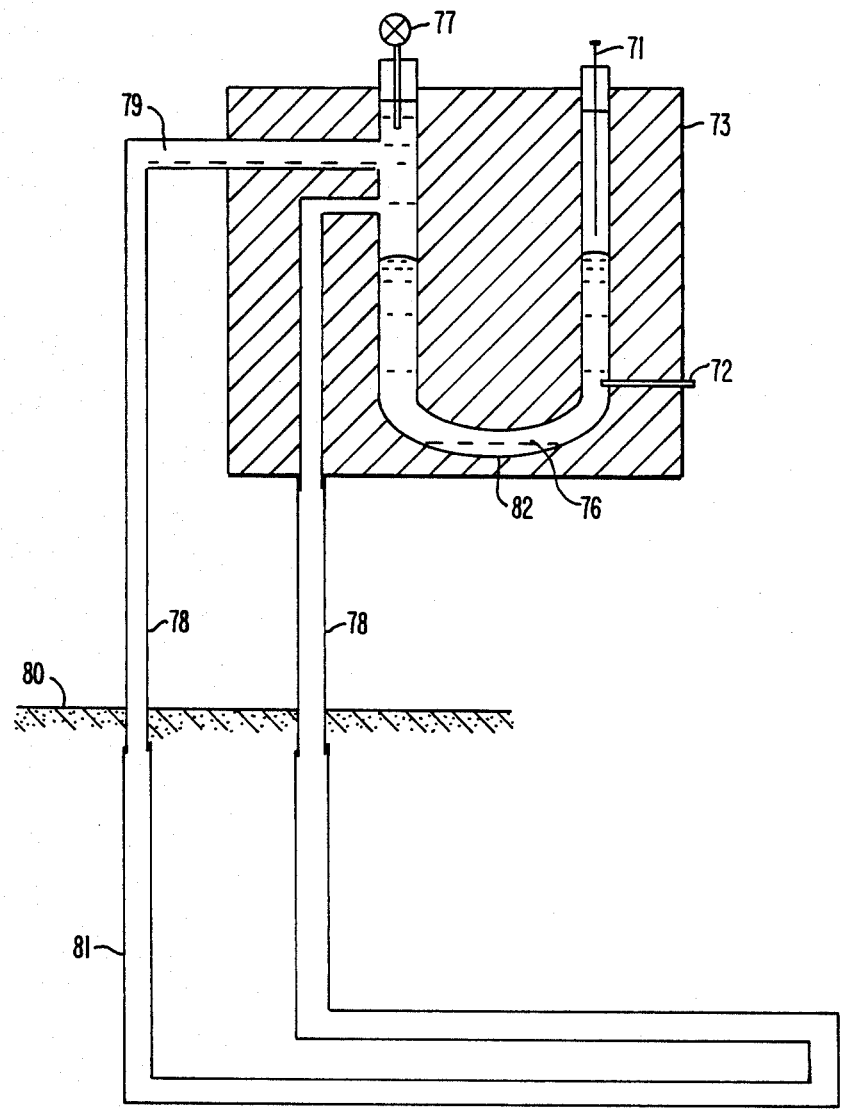
FIG._5.

OSMOTIC APPLICATIONS OF HOLLOW FIBERS

TECHNICAL FIELD

The present invention relates generally to fiber systems and more specifically to the use of semipermeable hollow fibers for osmotic measurement of gases, liquids and solids.

BACKGROUND OF THE INVENTION

Osmotic pressure refers to the pressure exerted by dissolved material in a solution on a semipermeable membrane that separates the solution from another solution or from a pure solute such as water. Such a membrane permits water to pass but is impermeable to dissolved substances. Water passes in an attempt to establish a chemical equilibrium between the two sides of the membrane. This passage of water is known as osmosis.

For a dilute solution, osmotic pressure is directly proportional to solute concentration as given by the Van't Hoff equation:

$$\pi = CRT$$

Where
$\pi$ = osmotic pressure
C = solute concentration
R = the gas constant
T = the absolute temperature.

At 25° C., the product $RT = 24.4$ liter.atm.mole$^{-1}$. Thus for a 1 molar solution, $x = 24.4$ atm. It can readily be seen that the determination of osmotic pressure ($\pi$), affords a convenient method for monitoring the solute concentration and hence the free water available in a biological system.

Osmotic concentration is generally expressed in osmoles. A solution which has an osmotic pressure of 22.4 standard atmospheres is said to have an effective osmotic concentration of one osmole per liter. For any individual substance, the osmole is defined as the weight in grams which gives rise to an osmotic pressure of 22.4 standard atmospheres when dissolved in one liter of solution.

Osmotic measurements can be used for a variety of purposes including molecular weight determination, monitoring physiological parameters, such as the amount of free water present in blood, urine and other biological fluids, determining the moisture content of a gas or a nourished liquid, as well as other industrial applications.

However, state of the art systems for determining the osmolarity of physiological solutions are unsuitable for routine clinical investigations in which rapid screening of large numbers of samples is usually required. Thus, osmotic pressure of physiological fluids such as blood, is generally determined indirectly, based on freezing point depression. This change in state can destroy red blood cells and thereby add soluble material to the plasma, changing the osmolar character of the blood and leading to inaccurate determinations.

The osmometer described in U.S. Pat. No. 3,479,864, although better suited for measuring physiological parameters, also suffers from several shortcomings. This osmometer contains a bed of beads in the measuring loop. Red blood cells can collect and become trapped on the beads and make cleaning difficult.

Current methods for determining the moisture content of a gas, i.e. to protect computers or other scientific equipment from excess moisture, also suffer from several drawbacks. These methods generally utilize a single point of information system. Thus, only the moisture content of a discrete area is determined which can be erroneously high or low.

Osmotic pressure determination also finds use in monitoring the moisture content of solids such as soils. State of the art methods for measuring soil moisture generally require that a dirt sample be removed from the ground, weighed, dried, weighed again and the wet weight compared to the dry weight. Alternatively, liquid can be sucked out of the sample and the volume determined. These methods, however, are time consuming, prone to error and do not discriminate between the presence of fresh water or salty water. Thus, a soil sample may be wet but not have any free water available for the plant.

Another method for determining soil moisture involves the use of a tensiometer. A tensiometer measures the energy status, or potential, of soil water. Tensiometers, however, suffer from several drawbacks. These devices operate in only a small fraction of the water potential range that is normally considered to be available for plant growth. Additionally, the tensiometer only measures water potential in a small volume of soil immediately surrounding the instrument. Further, tensiometers are expensive, fragile and difficult to install. Finally, root fibers can become entangled in these instruments and impede water potential measurement.

U.S. patent application Ser. No. 920,440, now, U.S. Pat. No. 4,805,343 incorporated herein by reference, discloses the use of a hollow fiber system as an osmotic valve for demand watering of plants. Such systems overcome many of the disadvantages of the prior art. It would therefore be desirable to utilize a hollow fiber system in other osmotic applications.

SUMMARY OF THE INVENTION

Accordingly, it is an object of the present invention to provide a system for osmotic measurement of liquids that can be used for rapid clinical screenings.

Another object of the subject invention is to provide a system for osmotic measurement of liquids that can be used in industrial applications.

A further object of the instant invention is to provide an improved system for determining the amount of moisture present in a gas.

Another object of the present invention is to provide a system for osmotic measurement of the free water content of a solid.

These and other objects of the invention are accomplished by the use of an osmometer having a semipermeable, hollow fiber filled with media. The fiber has a sealed end. A small amount of gas is present in the opposite end and is responsive to volume changes in the media. A pressure sensor is associated with the gas and measures pressure changes occurring in the fiber due to volume changes in the media.

In the preferred embodiment of the subject invention, the hollow fiber is composed of a hydrophilic material such as cellulose acetate or polyethylene and has asymmetric walls with a highly compact interior core and a loose outer matrix. A suitable cellulose acetate is available as an Eastman cellulose ester sold as Type CA-398-30.

The osmometer can be used for the determination of the moisture content of a gas, liquid or solid. When used to determine the osmotic pressure of a blood sample, the media present in the hollow fiber has preferably an osmolarity of approximately 320 milliosmoles.

Further objects and advantages of the subject invention will become apparent from the following detailed description when taken in conjunction with the drawings.

BRIEF DESCRIPTION OF THE DRAWINGS

FIG. 1 is a cross-sectional view of the subject osmometer.

FIG. 2 is an enlarged, cross-sectional view of a hollow fiber for use with the subject invention.

FIG. 3 shows the subject osmometer as used for osmotic determination of a physiological fluid such as blood.

FIG. 4 shows the subject osmometer as used for the osmotic determination of a liquid such as ketchup during its production.

FIG. 5 shows the subject osmometer as used for the osmotic determination of a solid such as soil.

FIG. 6 is a graph of the negative osmotic potential of water vapor over a salt solution.

DETAILED DESCRIPTION OF THE PREFERRED EMBODIMENTS

In accordance with the present invention, an osmometer is disclosed that permits osmotic measurement of a gas, liquid or solid. The apparatus utilizes a semipermeable, hollow fiber that allows water but not dissolved solids to pass. The hollow fiber is fabricated using a hot melt extrusion method or a melt spin process. U.S. Pat. No. 3,423,491 to McClain et al., the disclosure of which is hereby incorporated by reference, describes a process for the preparation of hollow fibers suitable for use with the present invention.

Specifically, a suitable hydrophilic powder is fed into an extruder such as a model 21663 extruder available from Dow Chemical Co. of Midland, Mich. The substance is heated until it becomes liquid. The heated liquid enters a dye and is shaped into a thin cylinder of fiber. Nitrogen is blown into the center of the dye so that a hollow core is formed in the cylinder. The hot cylinder then exits the extruder and enters a water bath. Next, the cylinder is fed onto a rate controlled pick up system. From there, the cylinder moves to a second fiber pick up system that is moving at a rate ten times as fast as the first pick up system. A 10 to 1 expansion or stretch of the fiber is therefore achieved. It will be noted that other stretch ratios will find use with the present invention.

As illustrated in FIG. 2, this method of fabrication results in a fiber 12 having asymmetric permeability, that is, the interior surface 14 of the fiber 12 is dense, highly compact and has relatively small pores. The exterior surface 16 of the fiber 12, on the other hand, consists of a relatively loose outer matrix with larger pores. It appears that such a structure results from the formation of gas bubbles during the fabrication process which develop and burst, leaving relatively large, funnel shaped cavities on the upper surface of the fiber 12, much in the manner of pancake batter as it is heated.

Such a structure favors the flow of water from the large pore side to the small pore side. Specifically, liquid on either side of the hollow fiber will have a hydraulic pressure dependent on several factors including the thickness of the fiber walls, hydrostatic pressure head, dissolved or suspended solids and the temperature of the liquids present. When the hydraulic pressure on one side of the fiber wall exceeds that on the other side by at least the osmotic pressure, water will pass through the wall to the side of the lower hydraulic pressure. Thus the fiber wall acts much as a pressure relief valve permitting water flow when the pressure rises sufficiently.

For example, when the osmolarity of the media component, $O_c$, is greater than the osmolarity of the exterior substance being measured, $O_e$, liquid will flow from the exterior of the fiber to the interior of the fiber. Conversely, when $O_c$ is less than $O_e$, liquid will flow from the interior of the fiber to the exterior. Finally, when a state of equilibrium exists such that $O_c$ is equal to $O_e$, no liquid will flow in either direction.

Fibers suitable for use with the present invention are those membranes that are permeable only to water but not to dissolved materials in solution. The material used should be bioresistant and insoluble in the solution to be monitored. Particularly useful are those fibers fabricated from hydrophilic powders such as one or more cellulose esters. For instance, cellulose mono-, di- and triacetates as well as cellulose propionate, cellulose butyrate, cellulose acetate propionate and cellulose acetate butyrate will find use with the present invention. Other suitable hydrophilic materials are disclosed in U.S. Pat. No. 3,423,491, and include cellulose ethers such as ethyl cellulose. Also useful are polyolefins such as polyethylene and polypropylene.

It has been found that fibers made from the cellulose acetates are susceptible to ultraviolet degradation but very stable underground. Thus, these fibers are particularly suited for underground purposes. Polyethylene tubing, on the other hand, finds use in above-ground applications where fibers will be exposed to ultraviolet light.

Fibers useful in practicing the present invention will generally have wall thicknesses ranging from approximately 1.0 to 5.0 mils with a ratio of wall thickness to outside tube diameter being between approximately 1:30 to 1:15. The length of the fibers is highly variable and can be from as little as one centimeter to several thousand meters, depending on the substance to be measured. The geometry of the fiber bundle can be any geometry that will not break or block the fiber. For instance, the fiber can be generally U-shaped (FIG. 1), coiled with one or more loops (FIG. 4) or linear (FIG. 3), depending on the system it is to be used in.

As illustrated in FIG. 1, after fabrication, one end of the hollow fiber 12, the sealed end 12a, is sealed by a method well known in the art such as mechanically with a plug 18, clamp or other device or by heat treatment or adhesive. The other end of the fiber, the pressure sensing end 12b, is not yet sealed. The hollow fiber is then filled with a media component 20. The media component used will vary depending on the substance to be measured. However, solvents of cellulose acetate, polyethylene or any other material component of the fiber should be avoided as should physical conditions that will melt the fiber. For example, formamide ($HCONH_2$) is a known solvent of cellulose acetate as are high molecular weight glycols when heated above 100° C. Water, on the other hand, poses no threat to the integrity of the fiber at any temperature.

The choice of a suitable media component would be well within the capability of one skilled in this art. Obviously, a NaCl aqueous solution is ideal when the osmolarity of a solid or a liquid containing water is determined. In addition, various polyelectrolytes which possess ionizable sodium as a salt can be employed as well as those various media found on pages D-127 to D-166, of the *Handbook of Physics & Chemistry*, 46th Edition, which include acetic acid, acetone, ammonium chloride, ammonium hydroxide and sodium hydroxide, the disclosure of which is incorporated herein by reference.

After the hollow fiber is filled with media, and while one end of the fiber remains unsealed, the system is calibrated so that the internal osmolarity is close in value to the anticipated osmolarity of the substance to be measured. In this way, there is not a great disparity between the internal media component and the sample, and measurement can proceed more accurately. This adjustment is made by placing the media component-filled hollow fiber in contact with a calibration medium. Liquid will flow into or out of the hollow fiber as explained above and the internal osmolarity will adjust to that of the external osmolarity.

Also present in the hollow fiber 12 is a relatively fixed small volume of gas 22. This gas, generally air and/or water vapor, is between 1/100 to 1/1000 of the total internal media volume. The gas 22 is located adjacent to the media component 20, in the pressure sensing end 12b of the hollow fiber 12. When media component 20 is water, water vapor is gas 22 which fills the free space as a result of the vacuum created when the water level drops within the hollow fiber. Located next to the gas volume 22, and sealed into the pressure sensing end 12b of the hollow fiber 12, is a pressure sensor 24. Thus, the final osmometer is a completely sealed system. The system can be permanently or removably mounted to a bracket, wall or stand. Any suitable pressure sensing transducer can be employed such as that supplied by Sen Syn of Sunnyvale, Calif.

The osmotic pressure is measured in the following fashion. The media-filled hollow fiber of the osmometer is placed in contact with the sample to be measured. Liquid will flow into or out of the hollow fiber according to the osmolarity of the core media and the osmolarity of the sample as described above. Thus, the volume of the core media will change as a direct function of the osmolarity of the sample. This volume change, in turn, will affect the gas volume in the hollow fiber. If the volume increases, the pressure exerted on the gas volume will increase and this pressure will be detected by the pressure sensor. If the volume of the core media decreases, the pressure will decrease and this will also be detected by the pressure sensor.

The subject osmometer is suitable for the measurement of gases, liquids and solids. For instance, the osmometer can be used for air moisture control, silicon chip cleaning and gas and moisture control in spray painting. Other industrial applications include monitoring the water content of blended drinks, wines, beers, sugar solutions, ketchup, milk and other emulsions and solutions. The water content of soil, stored grains, hay and other solids can also be monitored using the subject osmometer. Further, the present system provides a suitable means for continuously monitoring physiological parameters such as the water content of whole blood, serum, plasma or urine.

EXAMPLE I

Osmotic Determination of Whole Blood

The osmolarity of whole blood can be continuously monitored using the subject invention as depicted in FIG. 3. Cellulose acetate hollow fiber 55 was fabricated using the hot melt extrusion method described above. Whole blood was passed under pressure between approximately 60 to 190 mm Hg at 37° C. at inlet 50 employing a nitrogen gas pressure source 62. The whole blood was brought into contact with hollow fiber 55 loaded with a 280 milliosmole solution of NaCl corrected for 0.4 mg Heparin per 10 ml NaCl as an anticoagulating agent. This established a fail safe condition for the sterile osmotic media in the event of leakage flowing to the whole blood stream.

A measuring chamber was balanced to 280 osmolarity when the 280 milliosmole solution was used in the blood chamber against a 280 milliosmole solution used as the standard within the hollow fiber. Nitrogen gas emanating from source 62 was maintained over hollow fiber 55 to match blood flow pressure, i.e., between 60 to 190 mm Hg. If the flow of blood is stopped, the nitrogen gas will keep the blood and media under the same pressure.

The media within the hollow fiber at 280 osmolarity reaches an equilibrium with the whole blood sample and its osmolarity. If the osmolarity of the blood is lower than 280, then water flows from the blood to the media until the blood osmolarity equals that of the media, diluting the media from 280 milliosmoles while concentrating the blood to approach 280 milliosmoles. When the blood osmolarity is greater than that of 280 milliosmoles, water will flow from the media to the blood in an attempt to equalize the two liquids.

When water flows to the media, the level of fluid 59 in chamber 61 rises compressing the nitrogen gas found within chamber 61. This rise in liquid level can be read on a calibrated scale 60 as depicted in FIG. 3. Alternatively, a pressure transducer could be employed rather than the volume measuring device 61 depicted herein.

In operation, whole blood entering inlet 50 can flow continuously through the system exiting, at 51. The whole blood sample can be washed clear of blood feed line 53 and blood/fiber contact chamber 56 with a 280 milliosmole NaCl sterile standard containing 0.4 mg Heparin per 10 ml NaCl solution which is obviously used to standardize the liquid level in chamber 61 against scale 60. The temperature within the contact chamber 56 can be maintained by water jacket 58 which ideally maintains the liquid within contact chamber 56 at approximately 37° C.

EXAMPLE II

Osmotic Determination of Ketchup

The subject invention also finds use in several industrial applications including the osmotic determination of ketchup. The thickness of ketchup is a function of the free water present in the ketchup. It is therefore desirable to monitor osmolarity during the manufacture of ketchup so that thickness is consistent.

In this application, a hollow fiber is fabricated as in Example I. The fiber contains a NaCl solution having an osmolarity between approximately 1800 to 3600 and even as high as 7200, depending upon the ketchup being examined. The fiber is then mounted in a sample container 26. As shown in FIG. 4, hollow fiber 12 can be used in a coiled configuration for this purpose. The presence of a coil allows more surface area of the fiber to be exposed for osmotic measurement. The sample container 26 with the osmometer 10 is placed directly in the ketchup production line as illustrated in FIG. 4.

Specifically, tomato paste, salt, vinegar and other constituents of ketchup can be fed into a mixing vat 32 through feed lines 34. The blended ketchup exits mixing vat 32 via exit line 36. A sample of the ketchup present in exit line 36 passes into container 26 via an inlet (not shown). An osmotic measurement is made and the value is fed into a controller 38, such as a computer. If the osmolarity is within the desired range, the controller will signal a valve (not shown) in exit line 36 that will open to enable the ketchup to continue in the production line. If the osmolarity is not within the desired range, the ketchup will be directed back into mixing vat 32 via feedback line 40, where the osmolarity will be adjusted by the addition of the proper constituent. Thus, a continuous feedback monitoring system for the osmotic measurement of ketchup can be achieved. This system is suitable in other industrial applications as well.

EXAMPLE III

Osmotic Determination of Soil

The subject invention is also useful in the osmotic determination of solids, such as soil. Soil consists of several zones with varying water concentrations, ranging from complete water saturation, or 100% humidity, to zones with less humidity, until the surface of the soil is reached which will generally have the humidity of the air in the surrounding environment. Plants generally grow best when their roots are located in a relatively high humidity zone, such as 98% humidity, but not in the 100% humidity zone. Thus, an osmotic measuring device implanted in the soil at the root level can inform the user when to water the plant or plants being monitored.

Reference is made to FIG. 5 which depicts an osmometer assembly useful in the determination of the water concentration of soils. Below soil surface 80 is provided osmotic hollow fiber 81 consisting of cellulose acetate. Located within hollow fiber 81 and extending up through and within polyethylene connecting tubings 78 is a quantity of osmotic medium sodium chloride. The osmotic media in the hollow fiber can be adjusted to take up water in high moisture soil and to release it at any desired gradient of moisture drop in the soil vapor as relative humidity.

A manometer sensor is established by providing mercury 76 within U-shaped tubing 82. Electrode 72 is placed within the mercury while electrode 71 is generally situated above the mercury level. Bleed and media loading valve 77 is provided to equilibrate the mercury level. In operation, as dry soil takes water from the media osmotically, the mercury level drops breaking contact between electrode 71 and 72. When contact is broken, a relay can be established (not shown) to allow for the automatic watering of the soil. When watering has produced a soil moisture condition so that water now flows from the soil to the media, the mercury level will rise and establish contact between electrode 71 and 72. This can result in a turning off of the water supply.

The following table illustrates the moisture gradient/relatively humidity conditions for plant growth at the root zone:

TABLE III

| Soil Moisture Table & Diagram | | | | |
|---|---|---|---|---|
| Relative Humidity | Osmotic Potential | | | Soil Surface |
| 99% | −15 Bar | | → | ↑ |
|  | −10 Bar | −146 Psi | → | H₂O less |
| 99.5% | −6.0 Bar | −88 Psi | → | than salt |
| 100% RH | 0.0 Bar | −0.0 Psi | → | ↓ |

TABLE III-continued

| Soil Moisture Table & Diagram | | |
|---|---|---|
| Relative Humidity | Osmotic Potential | Soil Surface |
|  |  | ↑ |
|  |  | H₂O |
|  |  | Sat. |
|  |  | ↓ |
|  |  | Sub Surface |

This gradient will pass by the root zone depending on the amount and timing of watering and the resultant rise of the saturated water zone.

FIG. 6 illustrates the relationship between the osmolarity of the hollow fiber media needed to match the negative water vapor potential at osmotic hollow fiber loop 81. By adjusting the hollow fiber media osmolarity of, for example, a NaCl water solution, the sensor can be made to operate within the desired root water potential of −0 to −10 bar range.

Thus, an osmometer for use in the measurement of solids, gases or liquids has been disclosed. Although the subject invention has been disclosed with reference to preferred embodiments, it should be understood that various alternatives to the methods and materials herein disclosed may be employed in practicing the present invention. It is intended that the following claims define the invention, and that the materials and methods within the scope of these claims and their equivalents be covered thereby.

I claim:

1. An apparatus for determining osmotic pressure, said apparatus comprising:
   a semipermeable, hollow fiber, said fiber having a sealed end and a pressure sensing end;
   a media component contained within said fiber, said media component having a predetermined osmolarity;
   a relatively small amount of gas located adjacent said media component and distal to the sealed end of said fiber; and
   a sensor located in the sensing end of said fiber, said sensor in association with said gas, said sensor for measuring changes occurring within said fiber due to volume changes occurring in said media component.

2. The osmotic measuring apparatus of claim 1 wherein said fiber is comprised of one or more hydrophilic substances.

3. The osmotic measuring apparatus of claim 2 wherein said hydrophilic substance is selected from the group consisting of cellulose monoacetate, cellulose diacetate, cellulose triacetate, cellulose propionate, cellulose butyrate, cellulose acetate propionate, cellulose acetate butyrate, ethyl cellulose, polyethylene and polypropylene.

4. The osmotic measuring apparatus of claim 1 wherein said fiber includes asymmetric walls with a highly compact interior core and a loose outer matrix.

5. The osmotic measuring apparatus of claim 1 wherein said fiber has walls ranging in thickness from approximately 1.0 to 5.0 mils.

6. The osmotic measuring apparatus of claim 5 wherein said fiber has is characterized as having a ratio of wall thickness to outside diameter between approximately 1:30 to 1:15.

7. The osmotic measuring apparatus of claim 1 wherein said fiber has a length of at least 1 centimeter.

8. The osmotic measuring apparatus of claim 1 wherein said fiber is generally U-shaped.

9. The osmotic measuring apparatus of claim 1 wherein said fiber is present as a continuous coil.

10. The osmotic measuring apparatus of claim 1 wherein said fiber is substantially linear.

11. The osmotic measuring apparatus of claim 1 wherein is the osmotic pressure of blood is measured and said media component has an osmolarity of approximately 280 milliosmoles.

12. An apparatus for measuring the osmotic pressure of blood, said apparatus comprising:
- a semipermeable, hollow fiber having asymmetric walls, said fiber having a sealed end and a sensing end;
- a media component contained within said fiber, said media component having an osmolarity of approximately 280 milliosmoles;
- a relatively small amount of gas located adjacent said media component and distal to the sealed end of said fiber; and
- a sensor located in the sensing end of said fiber, said sensor in association with said gas, said sensor for measuring changes occurring within the contents of said fiber due to volume changes occurring in said media component.

13. The apparatus of claim 1 wherein said sensor is a pressure sensor for detecting pressure changes in said gas.

14. The apparatus of claim 1 wherein said sensor is a volume sensor for detecting volume changes of said media component.

* * * * *